United States Patent [19]
Riehm

[11] Patent Number: 5,426,473
[45] Date of Patent: Jun. 20, 1995

[54] SAFETY SPECTACLES WITH TEMPLE HINGE PROVIDING SIMULTANEOUS ADJUSTMENT OF EFFECTIVE TEMPLE LENGTH AND WIDTH BETWEEN TEMPLES

[75] Inventor: Merry S. Riehm, Buffalo, N.Y.

[73] Assignee: American Allsafe Company, Tonawanda, N.Y.

[21] Appl. No.: 145,962

[22] Filed: Oct. 29, 1993

[51] Int. Cl.$^6$ .......................... G02C 5/14; G02C 5/22
[52] U.S. Cl. ..................................... 351/121; 351/118; 351/148; 351/149; 351/153; 2/449; 2/450
[58] Field of Search ............... 351/111, 116, 118, 121, 351/140, 148, 149, 150, 153; 2/448, 449, 450, 451, 454; 16/228

[56] References Cited
U.S. PATENT DOCUMENTS

| | | | |
|---|---|---|---|
| D. 327,081 | 6/1992 | Nakamura et al. | D16/102 |
| 3,394,980 | 7/1968 | Dym | 351/118 |
| 3,713,732 | 6/1973 | Gooch | 351/153 |
| 3,787,113 | 1/1974 | Shedrow | 351/43 |
| 3,820,880 | 6/1974 | Burke | 351/121 |
| 4,017,165 | 4/1977 | Davis | 351/153 |
| 4,271,538 | 6/1981 | Montesi et al. | 2/450 X |
| 4,425,669 | 1/1984 | Grendo et al. | 2/436 |
| 4,526,448 | 7/1985 | Hanson | 351/153 |
| 4,544,245 | 10/1985 | Stansbury, Jr. | 351/118 X |
| 4,964,714 | 10/1990 | Weymouth, Jr. et al. | 351/111 X |
| 5,007,728 | 4/1991 | Magorien | 351/118 |
| 5,009,495 | 4/1991 | Williams | 351/153 |
| 5,009,496 | 4/1991 | Holtan, Jr. et al. | 351/156 |
| 5,074,655 | 12/1991 | Stanley et al. | 351/115 |

Primary Examiner—Anita Pellman Gross
Assistant Examiner—David R. Parsons
Attorney, Agent, or Firm—Dennis T. Griggs

[57] ABSTRACT

Adjustable size protective eyewear in the form of visitor safety spectacles have a moveable or adjustable hinge pin coupling between the temple sidebars and the lens frame. An opening in each side of the lens frame contains multiple hinge pin sockets which are aligned at an angle with respect to the lens frame such that movement of the hinge pins from socket to socket not only increases the distance between temple sidebars but also the effective length from the lens frame to the ear piece of the temple sidebar. This arrangement allows a single pair of adjustable safety spectacles to be used by a person of a given head size with the adjustability to fit over the user's prescription eyewear where the user requires the prescription eyewear in addition to the safety spectacles.

11 Claims, 5 Drawing Sheets

SAFETY SPECTACLES WITH TEMPLE HINGE PROVIDING SIMULTANEOUS ADJUSTMENT OF EFFECTIVE TEMPLE LENGTH AND WIDTH BETWEEN TEMPLES

FIELD OF THE INVENTION

This invention is related generally to protective eyewear which may be adjusted so as to be comfortably worn over corrective lens eyewear. In particular, the invention relates to an improved lens frame-to-temple sidebar hinge assembly which permits simultaneous adjustment of both left to right temple width and the effective lens frame-to-ear length of the temple sidebars.

BACKGROUND OF THE INVENTION

In most industrial environments, protective eyewear is required by state, federal or company regulations. In such environments, protective eyewear is worn to provide protection from projectiles and falling objects. Conventional eyewear provides some protection from oncoming flying materials and objects, but provides substantially no protection from foreign objects arriving from peripheral angles. Further, many conventional prescription eyeglasses are not shatterproof. Thus, when those lenses shatter upon the impact of a foreign object, the corrective lens glass will often add to the optical injuries.

There have been prior attempts to provide a "one size fits all" protective eyewear. Such eyewear typically provided a loose, unstable fit for some persons, and a very tight and uncomfortable fit for others requiring corrective lens eyewear or those having a physically larger head. Not only do head size variations cause comfort problems, distortion of the protective eye frames and shields may tend to cause gaps between the frame/shield and the head which allow penetration of flying objects into the protected area. The situation is aggravated by the presence of vision correcting eyewear beneath the protective eyewear.

Various custom-made safety spectacles are available which have shatterproof lenses, side shields, etc. However, it is not practical to provide such customized spectacles to a temporary visitor at an industrial site.

Description of the Prior Art

Conventional safety spectacles include the "one size fits all" protective eyewear which properly fits only a very small percentage of the population. Other prior art solutions include the use of large goggles with elastic bands that will completely enclose any prescription eyewear that the user may be wearing. Such goggles may be unacceptable to persons not requiring corrective eyewear on the basis that they are heavy and uncomfortable. This is especially true in high humidity situations when the goggles are not vented properly to prevent fogging and the accumulation of perspiration. Also, such goggles are typically expensive as compared to plastic safety spectacles.

A limited solution in the prior art for persons already wearing corrective eyewear is to add clip-on safety shields to the temple/ear pieces in the area of the lens body. However, this still leaves considerable unprotected space above and below the lens frames and the sidebar shields through which foreign objects may impinge upon the wearer's optical system. Further, many visitors using clip-on safety shields would still have the safety problem of a foreign object striking the non-strengthened corrective lens itself.

Although there have been various known attempts in the prior art to provide for adjustability of effective temple sidebar to earpiece length, there is no known simple adjustment concept known in the prior art for left temple sidebar to right temple sidebar width. Moreover, there is no known concept for simultaneously adjusting spectacle width and temple length.

OBJECTS OF THE INVENTION

The principal object of the present invention is to provide an inexpensive visitor safety spectacle that can be adjusted to accommodate visitors whether or not they must simultaneously wear corrective lens eyewear.

Another object of the present invention is to increase the effective length of the temple sidebar as the distance between temple side pieces is increased since as a general rule, a wider spacing between temple side pieces requires extra length to reach the wearer's ears.

Another object of the present invention is to provide adjustable protective eyewear that can be used in the same manner as and, if necessary, used in conjunction with prescription corrective eyewear.

A further object of the present invention is to make the size and comfort adjustment of safety spectacles easy to accomplish.

Still another object of the present invention is to eliminate any requirement of an elastic band encircling the wearer's head.

SUMMARY OF THE INVENTION

The foregoing objects are achieved according to the present invention by providing a hinge pin and a plurality of hinge pin sockets at the intersection of the viewing lens body and the hinged side piece/temple bars of the safety spectacles.

In a preferred embodiment, the plurality of sockets are interconnected in a slot with undulating sides. The slot may also be described as having a plurality of pivotal positions with deflectable and/or deformable projections or movement constraining sections between pivotal positions, to restrain accidental movement of the hinge pins from one pivotal position to another. The force necessary to move the hinge pins from one position to another is more than the force typically exerted upon the hinge pins by normal wearing of the safety devices by a visitor.

Proper positioning and alignment of the hinge pin sockets in the preferred embodiment cause the effective length of the temple sidebars to increase at the same time as the distance between left and right temple sidebars increases. This simultaneous alteration in distances occurs when (1) a line through the centers of the hinge pin sockets is at an obtuse angle with respect to an imaginary plane across the front of the lens frame body and (2) the temple/side pieces are at substantially right angles to the imaginary plane.

Operational features and advantages of the present invention will be understood by those skilled in the art upon reading the detailed description which follows with reference to the attached drawings.

DETAILED DESCRIPTION OF THE PREFERRED EMBODIMENT

Figure 1:
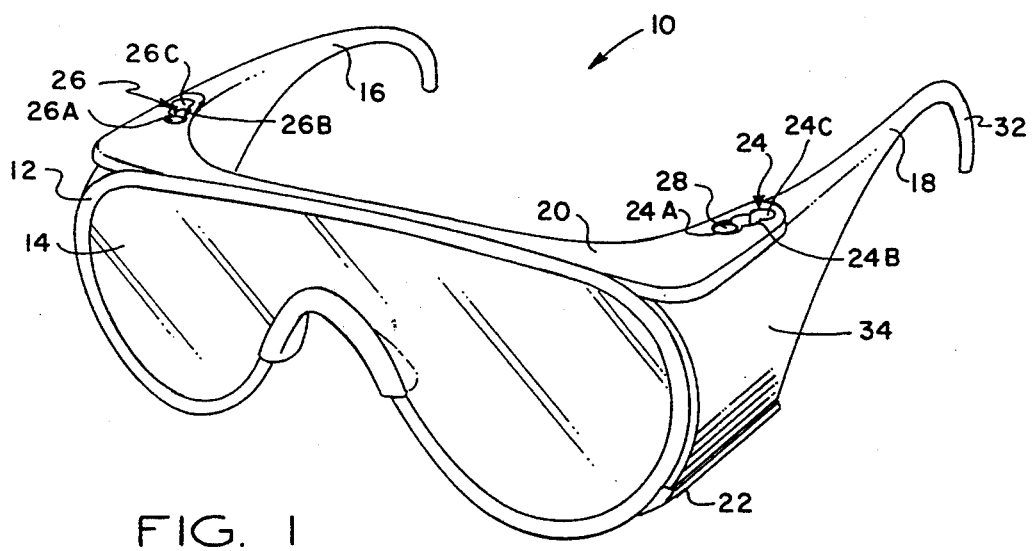
FIG. 1 is a perspective view of a pair of visitor safety spectacles incorporating a preferred embodiment of the size adjustment apparatus.

In the description which follows, like parts are indicated throughout the specification and drawings with the same reference numerals, respectively. The drawings are not necessarily to scale and the proportions of certain parts have been exaggerated to better illustrate details of the present inventive concept.

In FIG. 1, visitor safety spectacles or protective eyewear is generally shown as 10. A lens body, lens frame or frontal protective viewing body 12 encloses a viewing lens 14. Attached to one side of the lens frame 12 is a right temple bar 16, which includes a safety shield and a sidebar/earpiece. A similar temple bar, except designed for the left side of the users head is designated as 18. The lens frame 12 includes an upper frame shield 20 and a lower frame shield 22.

As illustrated in FIG. 1, there are a plurality of interconnected hinge pin sockets 24A, 24B, 24C forming an undulating slot 24 in the left portion of upper frame shield 20. As will be described in more detail later there is a constricted area or interference fit between each pair of hinge pin sockets to prevent inadvertent movement of a cooperating hinge pin from one socket to an adjacent socket. A similar slot 26 having interconnected hinge pin sockets 26A, 26B, 26C is shown in the right hand portion of upper frame shield 20. The slot 24 has forward, intermediate and rear hinge pin pivotal operating positions where a hinge pin 28 is shown occupying the forward pivotal position or hinge pin socket 24A within slot 24.

Figure 8:
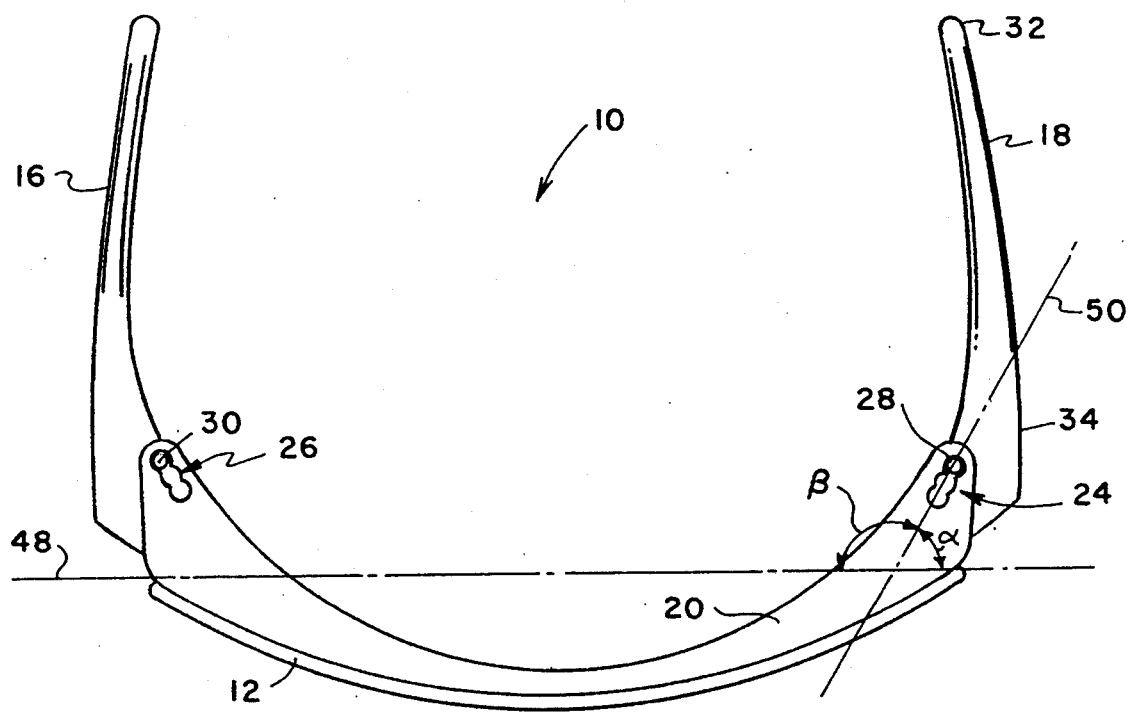
FIG. 8 is a top view of the spectacles of FIG. 1 when adjusted to the position shown in previous FIGS. 6 and 7.

In a preferred embodiment of the slot 24, adjacent hinge pin sockets may be viewed as describing a figure 8-type opening with a constricted region at the midpoint between adjacent hinge pin sockets being deformable to allow passage, upon the application of sufficient force, of pin 28 from one socket or operable hinge pin pivotal position to an adjacent socket or operable pivot point. Similar hinge pins and cooperating multiple hinge pin sockets 38A, 38B, 38C are formed in the lower frame shield 22. The temple bar 18 is shown with an ear piece or ear-engageable end 32 and a side safety shield portion 34.

Figure 2:
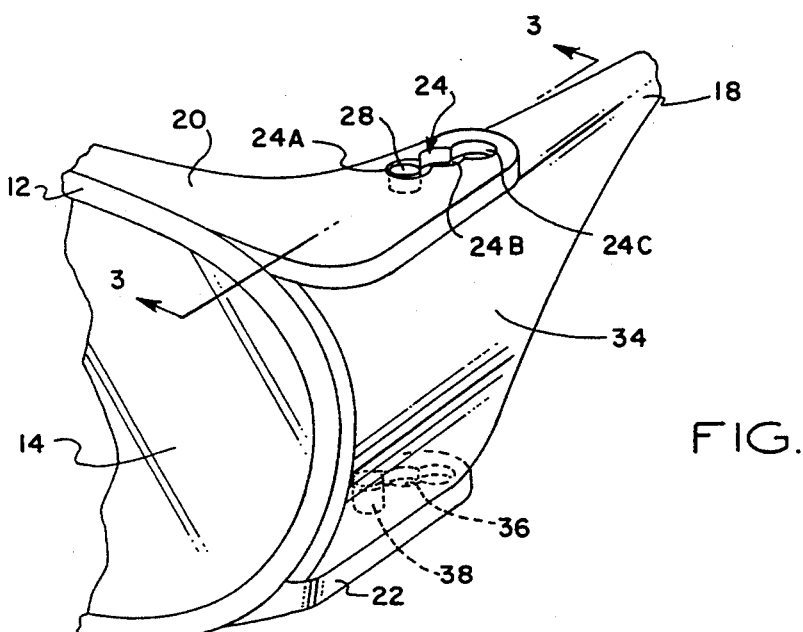
FIG. 2 comprises a fragmentary, enlarged view of a corner of the spectacles of FIG. 1 showing in greater detail the hinge pin and multiple socket apparatus as incorporated in both the upper and lower portions of the lens body.

In FIG. 2, a portion of FIG. 1 is shown along with an illustration of a lower hinge pin socket slot 36 in the lower frame shield 22 and a lower hinge pin 38 situated in the foremost hinge pin socket 36A or pivot point of slot 36. The parts 36 and 38 are shown in dash-line format since they are normally hidden from view at the angle shown.

Figure 3:
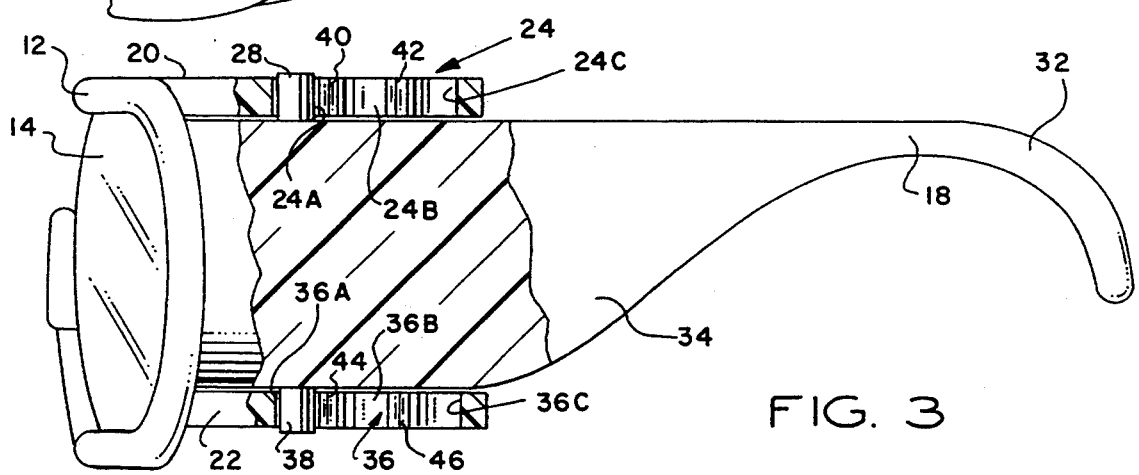
FIG. 3 is a side view of FIG. 1 with a break-away to better illustrate the pin and adjustable apparatus of FIGS. 1 and 2.

As defined in FIG. 2, FIG. 3 is a side view of the spectacles of FIG. 2 with emphasis on the left temple bar 18 and a cut-away into the upper and lower frame shields 20 and 22 to better show the hinge pins 28 and 38 along with the forward intermediate and rear-most hinge-pin sockets. Between the forward and middle socket of slot 24 there is shown the interference fit border section or deflectable projection 40. A further interference fit border section 42 is shown between the middle and rear-most hinge pin socket. Similar interference fit border sections or deflectable projections 44 and 46 are shown in lower frame shield 22.

Figure 4:
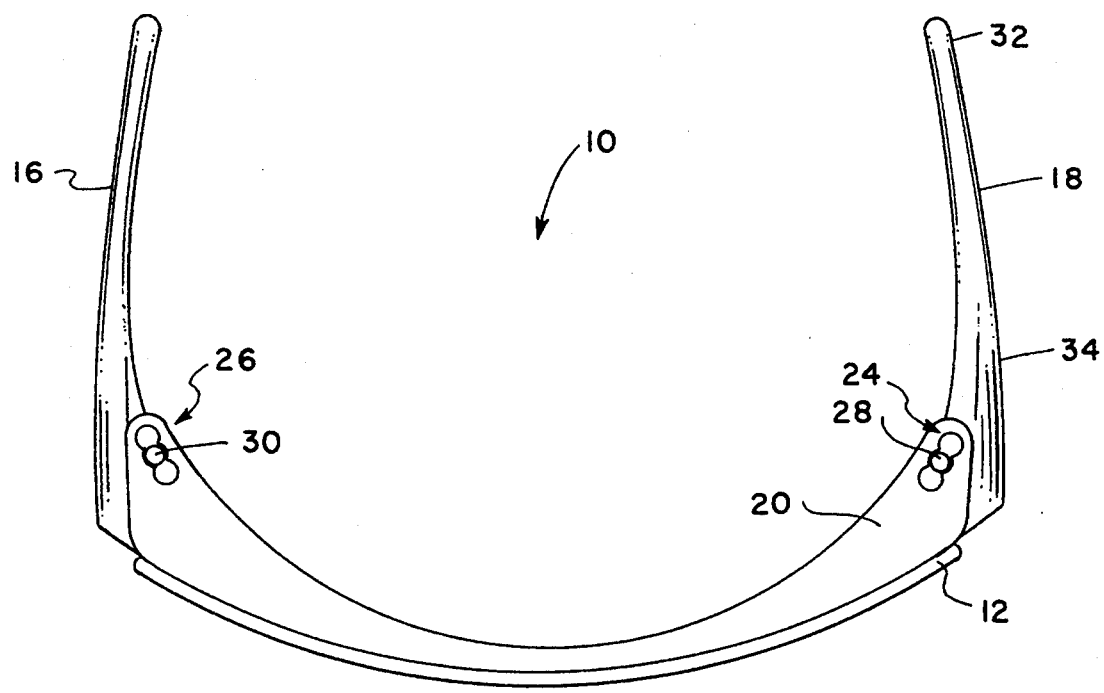
FIG. 4 is a plan or top view of the spectacles of FIG. 1 showing the temple sidebars in an intermediate hinge adjustment position as compared to the narrowest adjustment position illustrated in FIGS. 1-3.

FIG. 4 illustrates the safety spectacles 10 with both of the hinge pins 28 and 30 in the intermediate pivot positions or sockets of slots 24 and 26, respectively. In this position, the distance between temple sidebars 16 and 18 is wider than it is in the position shown in FIG. 1. Further, the distance between the ear piece end 32 of temple bar 18 is further from the front of the lens frame 12 than is the case in FIG. 1. The same holds for the distance from the unnumbered ear piece of temple sidebar 16.

Figure 5:
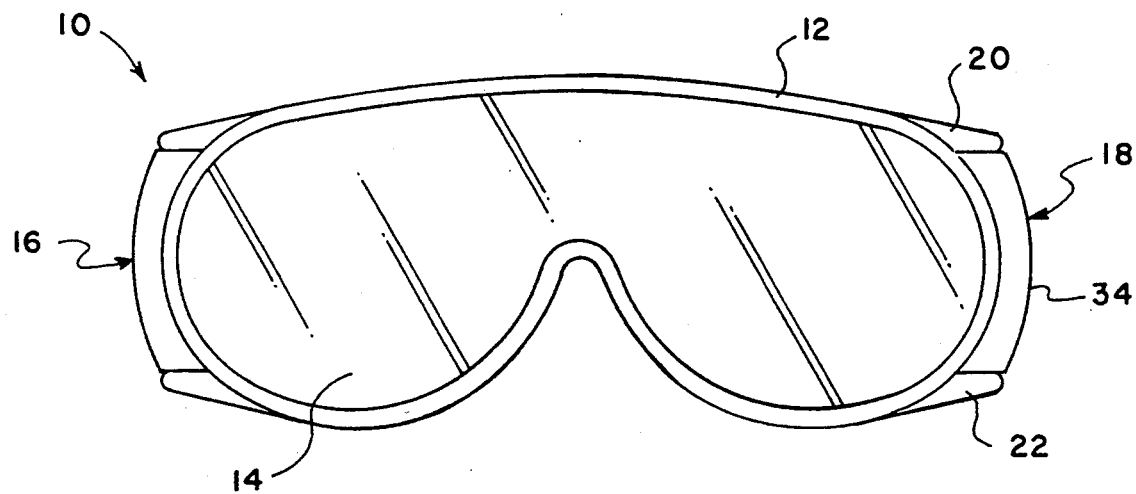
FIG. 5 is a front view of the safety spectacles of FIG. 1 when the hinge position is as shown in FIG. 4.

In frontal view FIG. 5, it can be clearly seen that the temple sidebars 16 and 18 extend a given distance beyond the edge of lens frame 12. It may be observed from the similar viewpoint of FIG. 9, where the hinge pins 28 and 30 are in the rearmost socket, the temple sidebars 16 and 18 extend even farther outward from the lens frame 12. While FIGS. 1 and 2 are not drawn from the same viewpoint as FIG. 5, it will be apparent by inspection of the drawings that the temple sidebars 16 and 18 are closer together when hinge pins 28 and 30 are in the forward socket than in the intermediate position as shown in FIG. 4 and FIG. 5.

Figure 6:
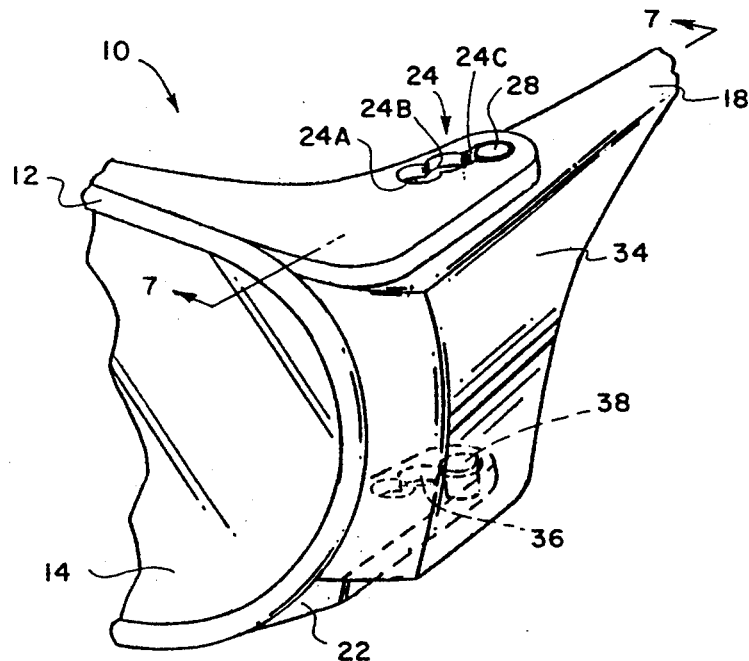
FIG. 6 is an enlarged view similar to that of FIG. 2 except that it shows the spectacles adjusted to the largest or most rearward position.

FIG. 6 illustrates the adjustment where hinge pins 28 and 38 of temple sidebar 18 are in the rear-most position of slots 24 and 36. It may be noted that shield 38 extends much further out beyond the edge of lens frame 12 in FIG. 6 than it does in a similar viewpoint drawing of FIG. 2 where the pins 28 and 38 are in the forward and innermost socket of slots 24 and 36.

Figure 7:
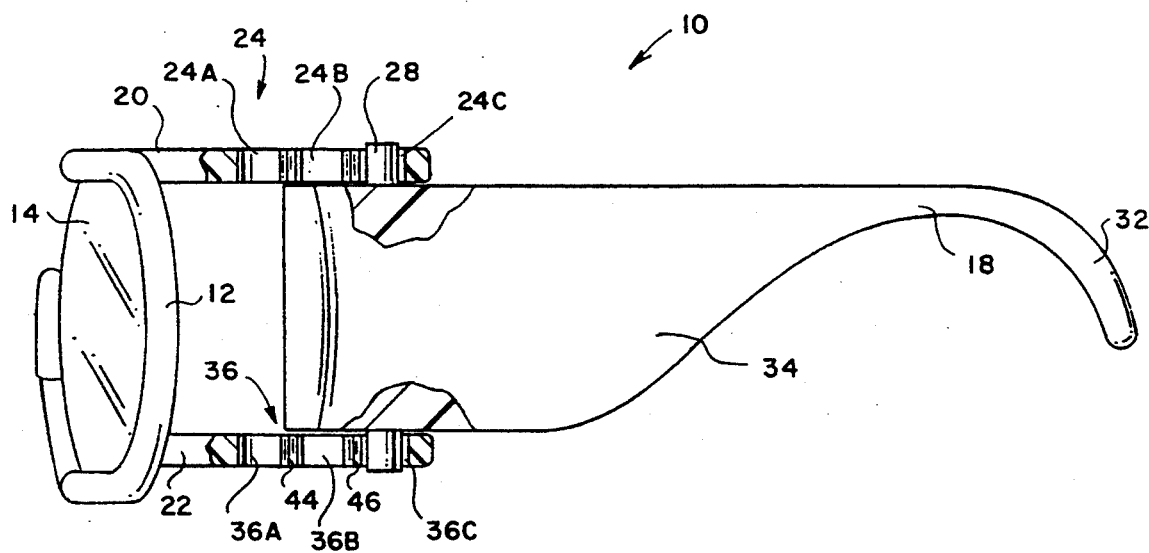
FIG. 7 is a side view of the spectacles of FIG. 1 when adjusted to the position of FIG. 6.

FIG. 7 is a side view of FIG. 6 with a break-away illustration of the slots 24 and 36 drawn in the same manner as FIG. 3 more clearly showing the pins 28 and 38 in the most rearward position of the adjustable slots.

FIG. 8 illustrates a top or plan view of the spectacles 10 with the temple bars 16 and 18 in their widest and most extended position. It will be noted that this view is similar to that of FIG. 4 which has the temples in the intermediate position. It will be apparent that in FIG. 8 there is more surface area to the frontal part of the shield 34 of temple bar or side piece 18. A dashed-line 48 is shown representing an imaginary plane through the lens frame 12. A further dashed-line 50 is drawn through the center of the various hinge pin sockets or pivotal points of slot 24.

The imaginary line 50 intersects the frontal plane 48 at either an acute angle $\alpha$ (alpha) or an obtuse angle $\beta$ (beta), depending on the way in which the angle is defined. If angle alpha is 45° (45 degrees), the temple bar 18 will extend laterally by the same amount that it extends longitudinally towards the ears upon each movement of the hinge pin 28 to successive rear hinge pin sockets or operable pivot points in slot 24. If both the left and right temple sidebars 18 and 16 are moved one position rearward, with the slot at an angle of 45°, the distance between temple sidebars 16 and 18 will increase twice as much as the distance from earpiece 32 is moved rearward. This is caused by the fact that both sidebars are moving outward from a central reference to produce an additive result.

Thus, if it is desired that the distance between temple sidebars increase by the same amount as the increase in effective length of earpiece 32 when the pins of both temple sidebars are moved one position rearward, the slot angle alpha must be 60°. If angle alpha is less than 45°, the movement of a hinge pin of a single temple sidebar from one socket to another is greater than the increase in effective length of the sidebar from frame to earpiece. Obviously, if angle alpha is greater than 45°, the reverse occurs.

Figure 9:
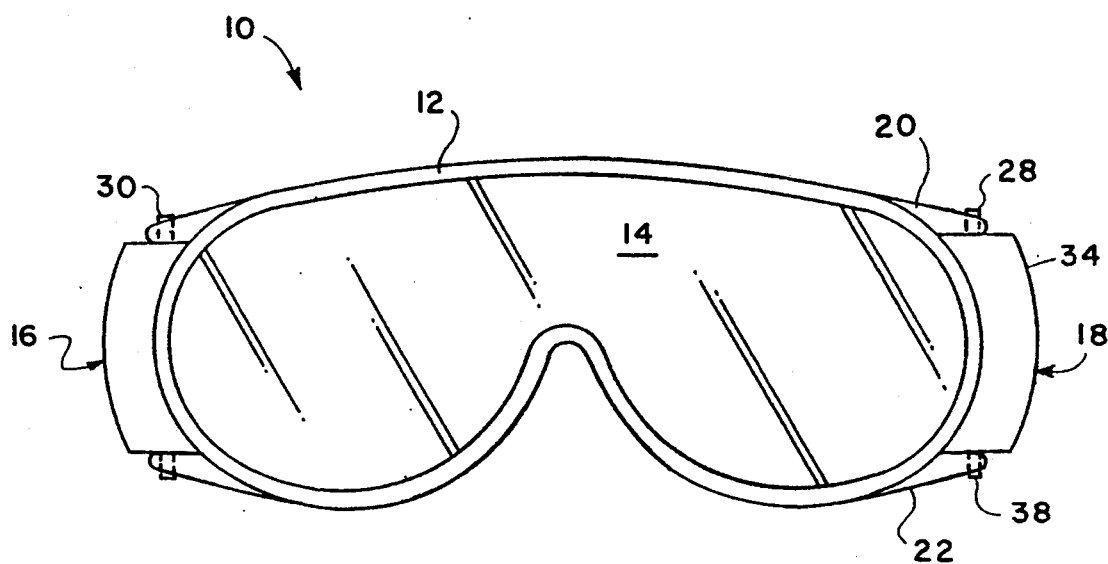
FIG. 9 is a front view of the spectacles when adjusted as illustrated in FIG. 8.

FIG. 9 is similar to FIG. 5 and shows the spectacles 10 with temple bars 16 and 18 in their most rearward and outward extended position as shown in FIG. 8.

Figure 10:
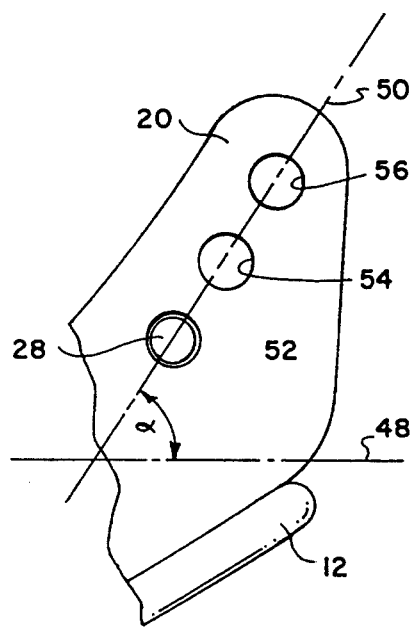
FIG. 10 comprises an enlarged view of a portion of the spectacles shown in FIG. 2 illustrating an alternate configuration for the socket portion of the hinge apparatus that does not require a deformable opening as used in the preferred embodiment.

FIG. 10 illustrates an alternate embodiment of the present concept where there are, as compared to the slot shown previously, unconnected hinge pin socket openings 52, 54 and 56 shown for use by the hinge pin 28. The temple sidebar 18 may be moved by flexing the upper and lower frame shields 20 and 22 in opposite directions to disengage pins 28 and 38 from the respective front opening and allow the same to be inserted into either of the middle or rear openings 54 and 56, as desired. In this embodiment, the material for frame shields 20 and 22 should be made of a resilient material which will spring back or otherwise return to the original shape and position after being deflected.

An arrangement of hinge pin sockets as shown in FIG. 10 is intended for use in situations where the spectacles may be subjected to rough handling and prevents the accidental repositioning of the lens frame under conditions of severe use. While the changing of pivot points in the embodiment of FIG. 10 would be more difficult than the preferred embodiment, it may be accomplished and a single manufacturing process and assembly line may be used for production of safety spectacles or other eyewear that can optionally be adjusted to any desired size.

Figure 11:
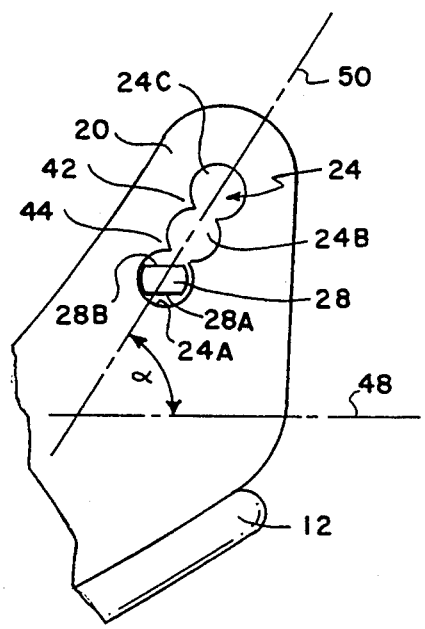
FIG. 11 illustrates the same portion of the spectacles as is illustrated in FIG. 10 and uses a slot concept with a hinge pin which is flattened on two sides to allow the adjustment when the temple sidebars are not in a user wearable position.

FIG. 11 illustrates another embodiment of the inventive concept where the hinge pin 28 is flattened on opposite sides 28A, 28B. In this embodiment, the projections or interference fit portions 40 and 42 need not be deflectable or deformable. This adjustment arrangement may be required if the upper or lower frame shield are made out of a rigid material such as steel. When using this adjustment arrangement, the temple bars may only be moved when they are in a folded condition. As may be observed, the hinge pin 28 is firmly retained in a given hinge socket when the temple bar 18 is substantially at 90° with respect to the lens frame 12. Preferably, the width of the flattened pin 28 is substantially equal to the distance between projections on opposite sides of the slot 24. The discussion with respect to upper frame shield 20 applies equally to lower frame shield 22 and its hinge pin and socket assembly.

Figure 12:
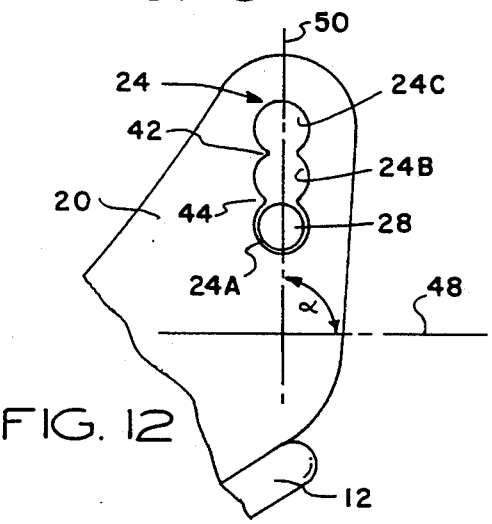
FIG. 12 illustrates the present inventive concept when it is desired that the adjustment be made only to the effective length of the ear piece.

FIG. 12 illustrates a further embodiment where the angle alpha is 90°. In such a situation, the temple bars may be adjusted only to increase the effective length from the ear piece 32 to the lens frame 12.

Figure 13:
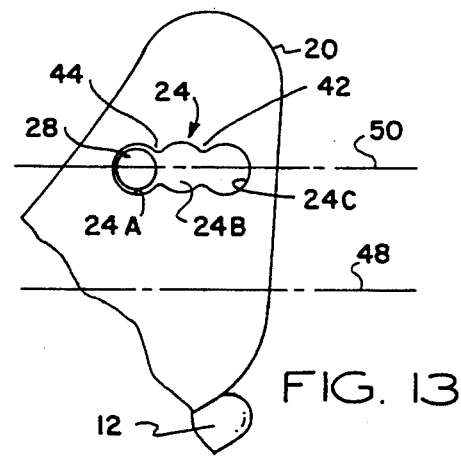
FIG. 13 illustrates the slot-type multiple socket adjustment mechanism when it is desired that the glasses be adjusted only as to distance between left and right temple sidebars.

FIG. 13 illustrates an arrangement where the line representing the axis of the sockets within slot 24 is parallel with the imaginary frontal plane 48 of the lens frame 12. In such a situation, there would be no increase in effective length of the ear piece 32 as the pin 28 is moved from position to position, but there would be changes in the distance between left and right temple sidebars 16 and 18.

It will be apparent that the basis of the present invention lies in having a readily adjustable series of hinge assembly positions interconnecting the two temple sidebars 16 and 18 on either side of a viewing lens frame 12 to modify the size of the visitor safety spectacles. A person with a given head size would typically require safety glasses of one size if he did not already wear corrective lenses and would have to wear a slightly larger size safety spectacles if he needed to wear the corrective lenses during a visit.

Figure 14:
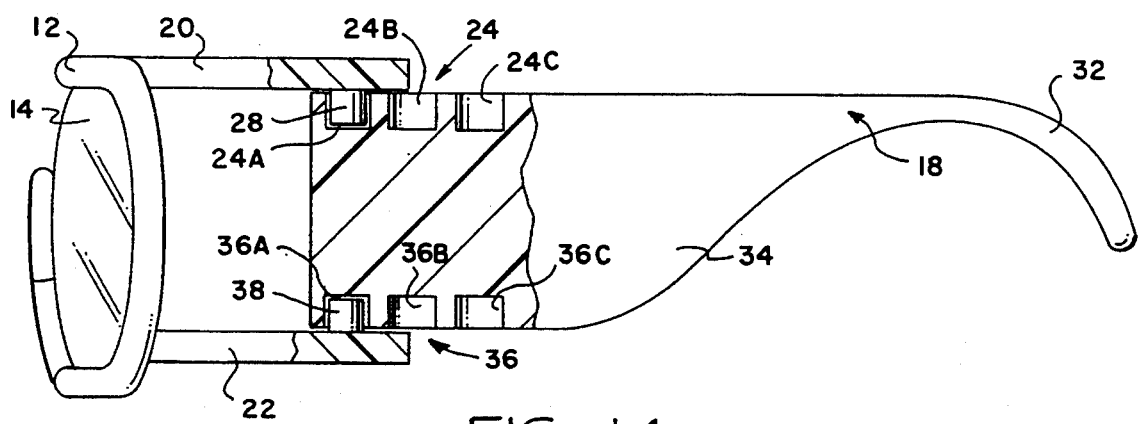
FIG. 14 is a side view similar to that of FIG. 7 showing an alternate arrangement of hinge design with the hinge pins incorporated in the frame shield and the hinge sockets being a part of the temple sidebar shield.

Although the preferred embodiment has the hinge pins on the temple bars 16 and 18, the hinge pins may very well be on the upper and lower frame shields 20 and 22 as illustrated in FIG. 14, where upper and lower cut-outs are provided in the shield portion 34 of temple sidebar 18 to house the multiple socket adjustment slots.

In the exemplary embodiment, the inventive concept has been applied to visitor safety spectacles. It is apparent that the concepts of the present invention may be used for any eyewear where adjustability is desired or required. Where a single manufacturing process can produce a finished product which may be adjusted to fit all situations, the product may be manufactured much less expensively as compared to producing many products of different sizes. Consequently, there may be instances where the present concept may be used simply to extend the length of the temple sidebar such as illustrated in connection with FIG. 12 or just to increase the width of the temples as illustrated in FIG. 13. Further, the alternative embodiment of FIG. 10 provides a more abuse-resistant adjustability than the preferred embodiment. The embodiment of FIG. 11 does not require that the material of the upper and lower frame shields 20 and 22 be deformable under pressure.

While a concept has been described which in a preferred embodiment is designed to allow visitor safety spectacles to be used by a person with a given head size, whether or not that person requires the use of prescription lens eyeglasses interior of the visitor safety spectacles, the concept may be applied to any eyewear and I wish to be limited not by the scope of the various embodiments illustrated but only by the scope of the appended claims, wherein I claim:

What is claimed is:

1. Safety spectacles comprising, in combination:
   first and second temple bars each having a sidepiece safety shield end and an ear engaging end;
   a lens body;
   hinge pins attached to one of the safety shield ends of each of said temple bars and each end of said lens body; and
   a plurality of hinge pin cooperating pivot points located in the other of the safety shield end of each of said temple bars and each end of said lens body, said cooperating pivot points being aligned along an angle relative to said lens body whereby the distance between temple bars is increased simultaneously with the increase of effective temple bar length upon adjustment of said cooperating pivot points in a predetermined direction.

2. Safety spectacles as defined in claim 1 wherein:
   the plurality of hinge pin cooperating pivot points are defined by a slot having undulating side walls which normally restrains movement of a hinge pin from one pivot point to an adjacent pivot point.

3. Protective eyewear comprising, in combination:
   a frontal protective viewing body including a lens and left and right side frame portions;
   left and right temple sidepiece shields disposed on the viewing body;
   pivot pin and socket combinations interconnecting said left and right shields with the frontal protective viewing body at said left and right side frame portions thereof; and
   at least one other socket for each pivot pin disposed such that said pivot pin is movable to said at least one other socket to simultaneously change relative left and right shield width distances and effective temple sidepiece length of said protective eyewear.

4. Protective eyewear as defined in claim 3 wherein:
   said viewing body is disposed in a plane disposed at an acute angle with respect to a line drawn through two of said sockets at each of said side frame portions of said viewing body, respectively.

5. Protective eyewear as defined in claim 3 wherein:
   said sockets are characterized by a continuous opening with deformable border portions disposed between operable pivotal positions of said pivot pin.

6. Protective eyewear as defined in claim 3 wherein:
   pivot pins project from the top and bottom of each of the left and right shields; and
   the left and right side frame portions each include at least one figure eight opening defining adjacent sockets for each pivot pin with deformable border portions substantially midway between operable positions of said pivot pin.

7. Protective eyewear as defined in claim 3 wherein:
   pivot pins project from the top and bottom of each of the left and right shields; and
   said viewing body includes a single opening having at least one figure eight opening configuration for permitting movement of a given pivot pin between sockets to adjust the distance between said shields.

8. The method of adjusting safety spectacles having a lens body and left and right temple side pieces comprising simultaneously increasing effective temple sidepiece length and the width between left and right temple sidepieces, comprising the steps of:
   forming a hinge pin on one of each of said temple sidepieces and said lens body;
   forming a series of cooperating hinge pivot sockets in the other of each of said temple sidepieces and said lens body where the series of cooperating hinge pivot sockets allow movement of the hinge pin with respect to the plane of the lens body; and
   moving each of the hinge pins to the pivot socket that provides the best fit for the wearer of the safety spectacles.

9. The method of making safety spectacles having a lens body and left and right temple side pieces which can simultaneously compensate in increased temple width and increased side piece length for wear in combination with a corrective vision eyepiece comprising the steps:
   forming hinge pins on the lens body end of the left and right temple sidepieces; and
   forming spaced apart openings, each opening comprising a series of at least two cooperating hinge sockets in said lens body where a pair of cooperating hinge sockets form a figure eight opening which are bordered by deformable projections to selectively restrain movement of a hinge pin from one socket to an adjacent socket.

10. Safety spectacles comprising, in combination:
    a lens frame;
    left and right temple sidebars each having an ear engaging portion; and
    adjustable hinging apparatus coupling said left and right temple sidebars to said lens frame, said hinging apparatus including a series of selectively engagable hinge pin sockets and hinge pins for permitting the distance between left and right earpieces to be increased simultaneously with an effective increase in earpiece length.

11. Safety spectacles as defined in claim 10 wherein:
    the angle of movement of said adjustable hinging apparatus, when the fit of the spectacles is being readjusted, resulting in the simultaneous lengthening of the ear engaging portion of the sidebars with respect to the lens frame as the distance between left and right sidebars is increased.

* * * * *